(12) United States Patent
Heidenfelder et al.

(10) Patent No.: US 6,387,355 B2
(45) Date of Patent: May 14, 2002

(54) USE OF SUNSCREEN COMBINATIONS COMPRISING, AS ESSENTIAL CONSTITUENT, AMINO-SUBSTITUTED HYDROXYBENZOPHENONES AS PHOTOSTABLE UV FILTERS IN COSMETIC AND PHARMACEUTICAL PREPARATIONS

(75) Inventors: Thomas Heidenfelder, Römerberg; Thorsten Habeck, Meckenheim; Thomas Wünsch, Speyer, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/805,727

(22) Filed: Mar. 7, 2001

(30) Foreign Application Priority Data

Mar. 15, 2000 (DE) .......................... 100 12 408

(51) Int. Cl.[7] .............. A61K 7/42; A61K 7/44; A61K 7/00
(52) U.S. Cl. ............ 424/59; 424/60; 424/400; 424/401
(58) Field of Search .............. 424/59, 60, 400, 424/401

(56) References Cited

U.S. PATENT DOCUMENTS

| 4,387,089 A | 6/1983 | DePolo ............ 424/59 |
| 5,576,354 A | 11/1996 | Deflandre ............ 424/59 |

FOREIGN PATENT DOCUMENTS

| AU | 79977/98 | 2/1999 |
| DE | 197 26121 | 12/1998 |
| DE | 19917906 | 10/2000 |
| EP | 087 098 | 8/1983 |
| EP | 251 398 | 1/1988 |
| EP | 416 837 | 3/1991 |
| EP | 514 491 | 11/1993 |
| EP | 850 935 | 7/1998 |
| EP | 916 335 | 5/1999 |
| EP | 933 376 | 8/1999 |
| FR | 79 27680 | 6/1980 |
| WO | 91/11989 | 8/1991 |
| WO | 99/66896 | 12/1999 |

Primary Examiner—Shelley A. Dodson
(74) Attorney, Agent, or Firm—Keil & Weinkauf

(57) ABSTRACT

Use of sunscreen combinations comprising as essential constituent, amino-substituted hydroxybenzophenones as photostable UV filters in cosmetic and pharmaceutical preparations.

14 Claims, No Drawings

USE OF SUNSCREEN COMBINATIONS COMPRISING, AS ESSENTIAL CONSTITUENT, AMINO-SUBSTITUTED HYDROXYBENZOPHENONES AS PHOTOSTABLE UV FILTERS IN COSMETIC AND PHARMACEUTICAL PREPARATIONS

The invention relates to the use of sunscreen combinations which comprise, as constituent which absorbs in the UV-A region, amino-substituted hydroxybenzophenones, and at least one other sunscreen which absorbs in the UV-A, region, UV-B region or in both regions, chosen from a group defined in detail below as photostable UV filter combination in cosmetic and pharmaceutical preparations for protecting the human epidermis or human hair against UV radiation, specifically in the range from 320 to 400 nm.

The sunscreens employed in cosmetic and pharmaceutical preparations have the task of preventing, or at least diminishing the consequences of, harmful effects of sunlight on the human skin. However, these sunscreens also serve to protect other ingredients from decomposition or degradation by UV radiation. In hair cosmetic formulations the aim is to reduce damage to the keratin fibers by UV rays.

The sunlight reaching the surface of the earth contains proportions of UV-B radiation (280 to 320 nm) and UV-A radiation (>320 nm), which are directly adjacent to the visible light region. The effect on the human skin is manifested, particularly in the case of UV-B radiation, by sunburn. Accordingly, the industry offers a relatively large number of substances which absorb UV-B radiation and thus prevent sunburn.

Dermatological investigations have now shown that UV-A radiation is also perfectly capable of causing skin damage and allergies by, for example, damaging the keratin or elastin. This reduces the elasticity and water storage capacity of the skin, i.e. the skin becomes less supple and tends to form wrinkles. The noticeably high incidence of skin cancer in regions where the sun's radiation is strong shows that damage to the genetic information in the cells is evidently also caused by sunlight, specifically by UV-A radiation. All these findings would therefore suggest the need to develop efficient filter substances for the UV-A region.

There is a growing demand for sunscreens for cosmetic and pharmaceutical preparations which can be used in particular as UV-A filters and whose absorption maxima ought therefore to be in the range from about 320 to 380 nm. In order to achieve the required effect using the minimum amount, sunscreens of this type ought additionally to have a high specific absorbance. Sunscreens for cosmetic products must also meet a large number of other requirements, for example good solubility in cosmetic oils, high stability of the emulsions produced with them, toxicological acceptability, and low intrinsic odor and low intrinsic color.

Another requirement which sunscreens must meet is adequate photostability. However, this is only inadequately ensured, if at all, with the UV-A-absorbing sunscreens hitherto available.

French Patent No. 2 440 933 describes 4-(1,1-dimethylethyl)-4'-methoxydibenzoylmethane as a UV-A filter. It is proposed to combine this specific UV-A filter, which is sold by GIVAUDAN under the name "PARSOL 1789", with various UV-B filters in order to absorb all UV rays having a wavelength from 280 to 380 nm.

However, this UV-A filter does not have sufficient photochemical stability, when used alone or in combination with UV-B filters, to ensure sustained protection of the skin during sunbathing for prolonged periods, which means that repeated applications at regular and short intervals are required if effective protection of the skin from all UV rays is desired.

For this reason, EP-A-0 514 491 discloses the stabilization of the insufficiently photostable UV-A filters by adding 2-cyano-3,3-diphenylacrylic esters which themselves act as filters in the UV-B region.

It has furthermore already been proposed in EP-A-0 251 398 and EP-A-0 416 837 to combine chromophores absorbing UV-A radiation and UV-B radiation into one molecule using a linker. This has the disadvantage that firstly a free combination of UV-A and UV-B filters in the cosmetic preparation is no longer possible, and that difficulties in the chemical linkage of the chromophores allow only certain combinations.

It is an object of the present invention to propose sunscreens for cosmetic and pharmaceutical purposes which absorb in the UV-A region with high absorbance, which are photostable, have low intrinsic color, i.e. a sharp band structure, and are soluble in oil or water depending on the substituent.

We have found that this object can be achieved advantageously by certain sunscreen combinations.

Accordingly, this object is achieved according to the invention by the use of sunscreen combinations comprising A) compounds absorbing essentially in the UV-A region and B) further compounds absorbing in the UV-A region, in the UV-B region and over both regions where the constituents (A) absorbing in the UV-A region comprise effective amounts of at least Aa) one hydroxybenzophenone of the formula I

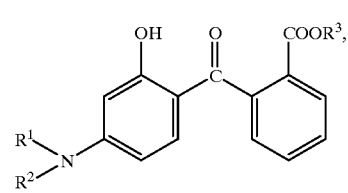

I in which
R$^1$ and R$^2$ independently of one another are hydrogen, C$_1$–C$_{20}$-alkyl, C$_3$–C$_{10}$-cycloalkyl or C$_3$–C$_{10}$-cycloalkenyl, where the substituents R$^1$ and R$^2$, together with the nitrogen atom to which they are bonded, can form a 5- or 6-membered ring and
R$^3$ is C$_1$–C$_{20}$-alkyl
and optionally additionally
Ab) 4,4'-diarylbutadienes of the formula II

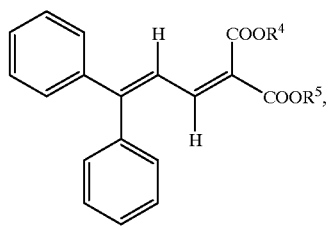

II in which
R$^4$ and R$^5$ independently of one another are hydrogen, C$_1$–C$_{20}$-alkyl, C$_3$–C$_{10}$-cycloalkyl or C$_3$–C$_{10}$-cycloalkenyl, and the constituents B) an effective amount of at least one compound chosen from the group consisting of Ba) dibenzoylmethane compounds of the formula III

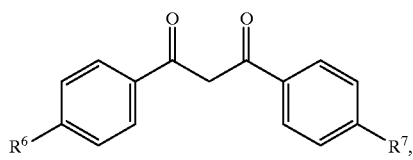

III in which
R⁶ is $C_1$–$C_{12}$-alkyl and
R⁷ is hydrogen, $C_1$–$C_{12}$-alkyl or $C_1$–$C_{12}$-alkoxy, Bb) triazine derivatives of the formula IV

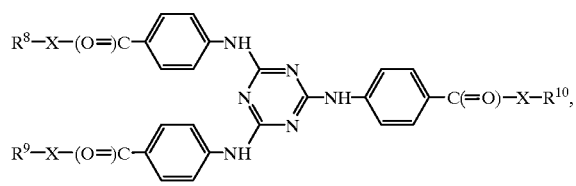

IV in which
$R^8$ to $R^{10}$ independently of one another are optionally SpSil, where Sp is a spacer and Sil is a silane, oligosiloxane or polysiloxane radical,
X is the divalent radical
—O— or

where
$R^{11}$ is hydrogen or optionally substituted $C_1$–$C_{20}$-alkyl, $C_5$–$C_{10}$-aryl or $C_5$–$C_{10}$-heteroaryl, Bc) the triazine derivative of the formula V

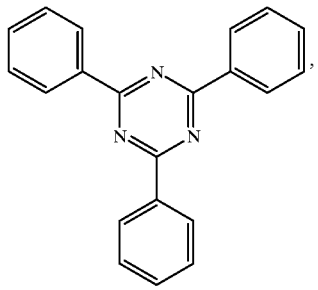

V in which at least one o-hydroxyl group and at least one p-alkoxy group having 1 to 20 carbon atoms are bonded to the phenyl rings, Bd) the benzotriazole derivative of the formula VI

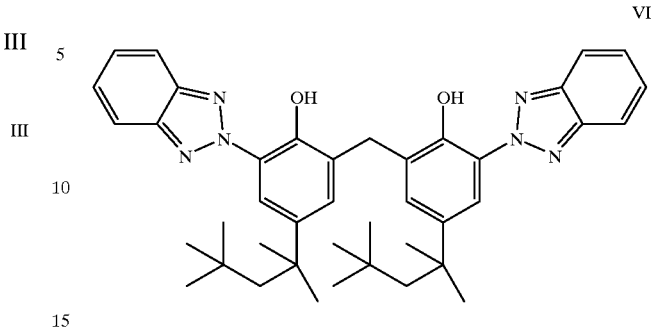

VI

Be) the benzimidazole derivative of the formula VII

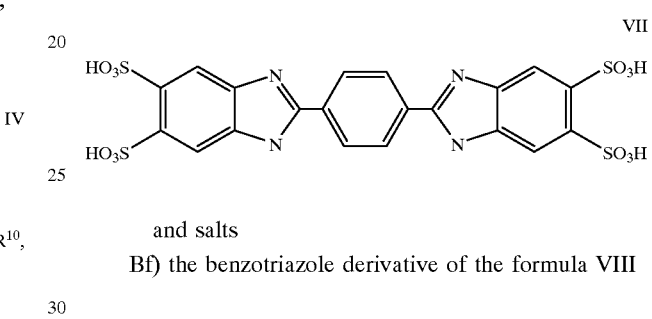

VII and salts

Bf) the benzotriazole derivative of the formula VIII

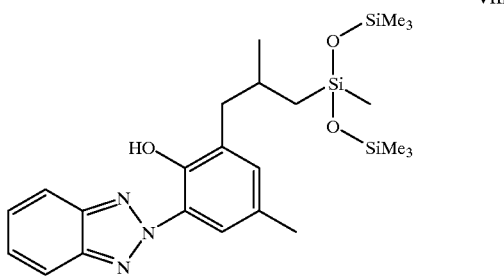

VIII

Bg) o,o',p,p'-tetrahydroxybenzophenone of the formula IX

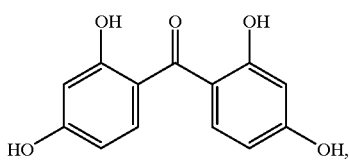

IX

Bh) an organosiloxane benzalmalonate of the formula Xa

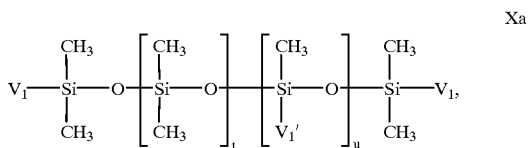

Xa in which
V₁' is the group

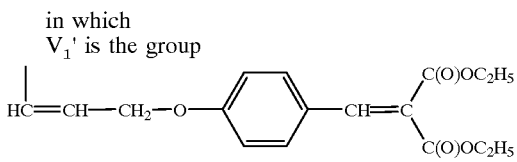

V₁ is a methyl group or V₁', or of the formula Xb

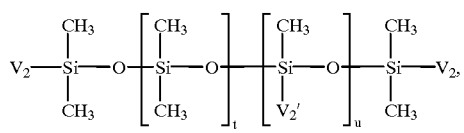

Xb in which V₂' is the group of the structure

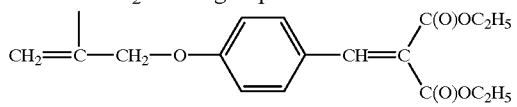

V₂ is a methyl group or V₂',
or mixtures of compounds of the formulae Xa and Xb, where t is a value up to 100 and u is a value up to 20, with the proviso that u=0, when V₁=V₁' and/or V₂=V₂', and u is a value from 1 to 20, when V₁=CH₃ and/or V₂=CH₃,
as photostable UV filters in cosmetic and pharmaceutical preparations for protecting human skin or human hair against solar rays, optionally together with other compounds which absorb in the UV region and which are known per se for cosmetic and pharmaceutical preparations.

The sunscreen combination of the compounds (A) and (B) can be used alone or in combination with other compounds which absorb in the UV range, although at least effective amounts of the compounds (A) and (B) should be present in the sunscreen preparations. "Effective amounts of the compounds (A) and (B)" means generally in each case at least 0.2% by weight, in each case based on the cosmetic preparation.

In the sunscreen combinations according to the invention, the amount of compounds which absorb in the UV-B region usually predominates. Accordingly, the content of the compound (A) which absorbs in the UV-A range is generally 5 to 50% by weight, preferably 10 to 25% by weight, in each case based on sunscreen combination of (A) and (B).

The combinations of sunscreens (A) and (B) according to the invention have synergistic effects in sun protection action inasmuch as the protective action of the combinations exceeds the sum of the action of the constituents.

The component Aa) which forms the essential constituent of the sunscreen combination is the subject of the previous German Patent Application DE-A 11917906 and is described therein, including the preparation, in detail.

Suitable alkyl radicals R¹, R² and/or R³ are branched or unbranched C₁–C₂₀-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl or 2-ethylhexyl.

Preferred alkyl radicals for R¹, R² and R³ are methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl and 2-ethylhexyl.

Preferred C₃–C₁₀-cycloalkyl radicals for R³ are cyclopropyl, cyclopentyl and cyclohexyl.

The optional compounds Ab), i.e. 4,4'-diarylbutadienes of the formula II,

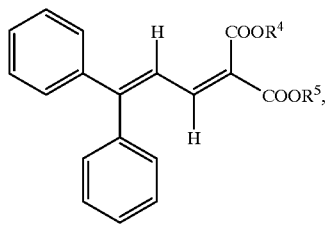

II are known from EPA 916 335. The substituents R⁴ and/or R⁵ are preferably C₁–C₈-alkyl and C₅–C₈-cycloalkyl and very particularly neopentyl.

The compounds (B) are all known and are characterized below in more detail:

(Ba)

The compounds of the formula III are known from FR 2440933. A suitable and preferred compound of the formula III is p-methoxy-p'-t-butyl-dibenzoylmethane (R⁶=methoxy, R⁷=t-butyl).

(Bb)

Compounds of the formula IV where R⁸ to R¹⁰ are alkyl, aryl or heteroaryl are known from EP-A 0796851, EP-A 0087098 and EP-A 0850935. Suitable alkyl radicals are, in particular, straight-chain or branched C₁ to C₁₂ radicals, in particular C₁ to C₈ radicals. Aryl radicals are, for example, phenyl or naphthyl radicals, in particular phenyl radicals. Suitable heteroaryl radicals are single or fused ring systems having one or more heteroaromatic 3- to 6-membered rings. As heteroatoms, one or more nitrogen, sulfur and/or oxygen atoms may be present in the ring or ring system.

Compounds of the formula IV with the meaning SpSil are known from EPA 0 933 376.

The term spacer for Sp means in this connection a bivalent branched or unbranched C₃–C₁₂-alkylene chain or alkenylene chain which links the silane, oligosiloxane or polysiloxane moiety to the triazine radical.

Examples of a C₃–C₁₂-alkylene chain are propylene, 2-methylpropylene, butylene, pentylene and hexylene.

Examples of a C₃–C₁₂-alkenylene chain are 2-propen-2-ylene, 2-methyl-3-propenylene, 3-buten-3-ylene and 4-penten-4-ylene.

Preferred spacers are —(CH₂)₃—, —(CH₂)₄—, —(CH₂)₅—, —[CH(CH₃)]—(CH₂)—, —(CH₂)₂—CH=CH—, —C(=CH₂)—CH₂—, —C(=CH₂)—(CH₂)₂—O—(CH₂)₄—, —(CH₂)₄—O—(CH₂)₂—.

The term silanes in this connection stands for a radical SiR¹²R¹³R¹⁴, in which R¹², R¹³ and R¹⁴, independently of one another, are C₁–C₆-alkyl, C₁–C₆-alkoxy or phenyl.

Examples which may be mentioned are: Si(CH₂–CH₃)₃, Si(CH₂—CH₂—CH₃)₃, Si(isopropyl)₃, Si(tert-butyl)₃, Si(tert-butyl)(CH₃)₂, Si(CH₃)₂ (hexyl), Si(OCH₃)₃, Si(OEt)₃, SiPh₃.

The term oligosiloxanes means a radical from the group of the general formula, consisting of SiR¹⁵ₘ(OSiR¹⁵₃)ₙ where m=0, 1 or 2; n=3, 2 or 1 and m+n=3, R¹⁵—[Si(R¹⁵)₂—O—]ᵣ—Si(R¹⁵)₂—A and R¹⁵—[Si(R¹⁵)₂—O—]ᵣ—Si(A) (R¹⁵)—O—Si(R¹⁵)₃, in which A is a chemical bond or a spacer and R¹⁵ is a C₁–C₆-alkyl radical or phenyl radical, and r is a value from 1 to 9.

The term polysiloxane includes, for example, a radical from the group of the general formula, consisting of A—[Si $(R^{16})_2—O]_s—Si(R^{16})_2—A$ or $(R^{16})_3—Si—[O—Si(R^{16})_2]]_t—[O—Si(R^{16})(A)]_q—Si(R^{16})$ in which A is a chemical bond or a spacer and $R^{16}$ is a $C_1$-$C_6$-alkyl radical or phenyl radical, s and t are values from 4 to 250 and q is a value from 1 to 30.

Suitable compounds of the formula IV are preferably the triazine compounds of the formula IVa

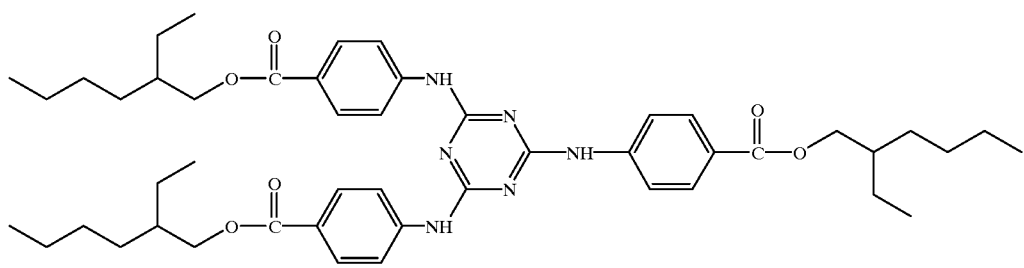

IVa or of the formula IVb

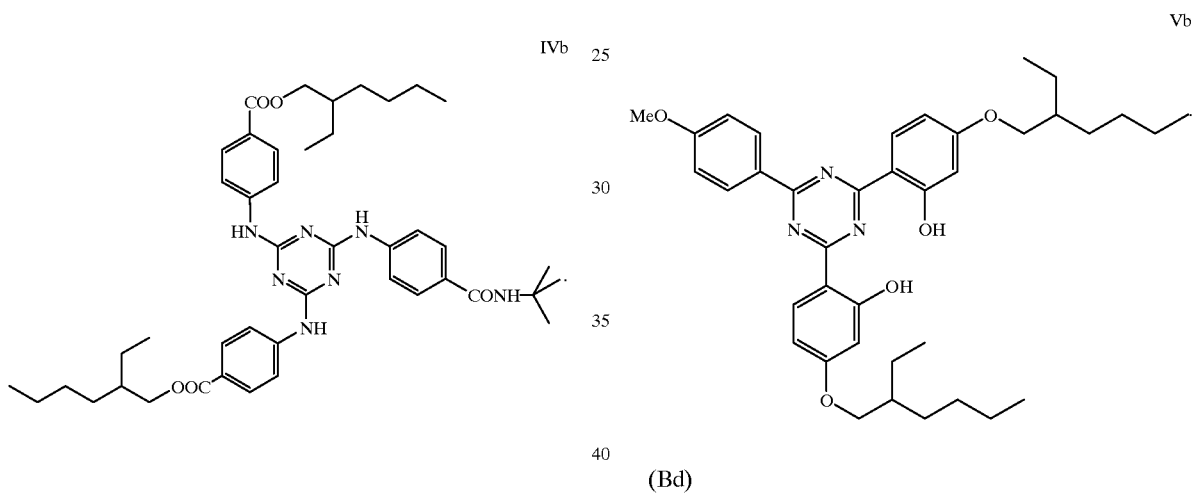

IVb (Bc)

Triphenyltriazines of the formula V substituted by at least one o-hydroxyl group and at least one p-alkoxy group are known from WO 99/66896.

In particular, triphenyltriazines of the formula Va are suitable

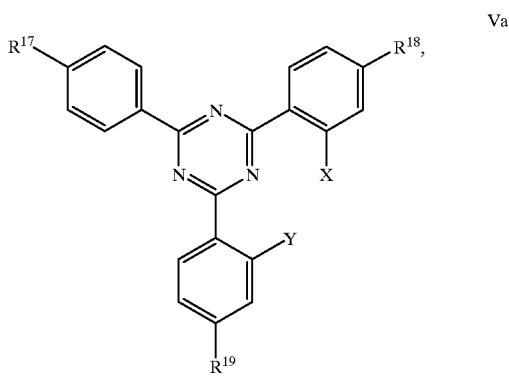

Va in which X is hydrogen or a hydroxyl group and Y is a hydroxyl group, $R^{17}$ is hydrogen or alkoxy having 1 to 12 carbon atoms and $R^{18}$ and $R^{19}$ are alkoxy having 1 to 12 carbon atoms.

Particular preference is given to the compound of the formula Vb

Vb (Bd)
The compound of the formula VI has the CAS No. 103597-45-1.
(Be)
The compound of the formula VII has the CAS No. 180898-37-7.
(Bf)
The compound of the formula VIII has the CAS No. 155633-54-8.
(Bg)
The compound of the formula IX has the CAS No. 131-55-5.
(Bh)
The compounds of the formulae Xa and Xb are known from EP-A 0920859.
Of the compounds of the formulae Xa and/or Xb those with the CAS numbers 208391-15-5, 208391-15-5D, 177955-90-7, 177955-90-7D and 177995-90-7DP are particularly suitable.

In the sunscreen combinations to be used according to the invention, it is possible for not only individual compounds (Ba) to (Bh) to be present, but also mixtures of two or more of these compounds.

The present invention further relates to cosmetic and pharmaceutical preparations which have 0.1 to 10% by weight, preferably 1 to 7% by weight, based on the total amount of cosmetic and pharmaceutical preparation, of a sunscreen combination comprising A) compounds absorbing essentially in the UV-A region and B) further compounds absorbing in the UV-A region, in the UV-B region and over both regions, where the constituents (A) absorbing in the UV-A region comprise effective amounts of at least Aa) one hydroxybenzophenone of the formula I

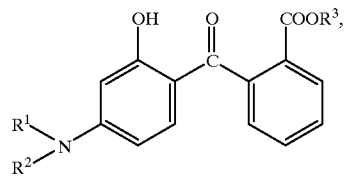

I in which

R$^1$ and R$^2$ independently of one another are hydrogen, C$_1$–C$_{20}$-alkyl, C$_3$–C$_{10}$-cycloalkyl or C$_3$–C$_{10}$-cycloalkenyl, where the substituents R$^1$ and R$^2$, together with the nitrogen atom to which they are bonded, can form a 5- or 6-membered ring and R$^3$ is C$_1$–C$_{20}$-alkyl and optionally additionally Ab) 4,4'-diarylbutadienes of the formula II

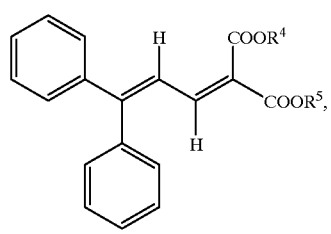

II in which

R$^4$ and R$^5$ independently of one another are hydrogen, C$_1$–C$_{20}$-alkyl, C$_3$–C$_{10}$-cycloalkyl or C$_3$–C$_{10}$-cycloalkenyl and as constituents B) an effective amount of at least one compound chosen from the group consisting of Ba) dibenzoylmethane compounds of the formula III

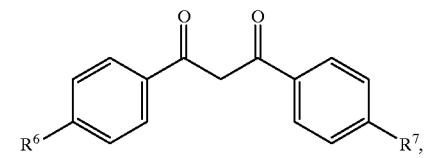

III in which

R$^6$ is C$_1$–C$_{12}$-alkyl and

R$^7$ is hydrogen, C$_1$–C$_{12}$-alkyl or C$_1$–C$_{12}$-alkoxy,

Bb) triazine derivatives of the formula IV

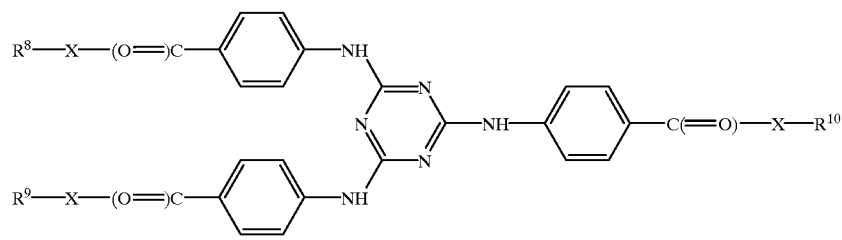

IV in which

R$^8$ to R$^{10}$ independently of one another are optionally substituted C$_1$–C$_{20}$-alkyl, C$_5$–C$_{10}$-aryl, C$_5$–C$_{10}$-heteroaryl or SpSil, where Sp is a spacer and Sil is a silane, oligosiloxane or polysiloxane radical, X is the divalent radical —O— or

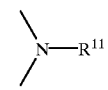

where

R$^{11}$ is hydrogen or optionally substituted C$_1$–C$_{20}$-alkyl, C$_5$–C$_{10}$-aryl or C$_5$–C$_{10}$-heteroaryl, Bc) triazine derivatives of the formula V

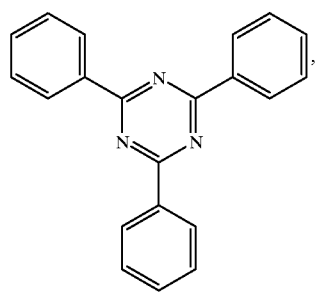

V in which at least one o-hydroxyl group and at least one p-alkoxy group having 1 to 20 carbon atoms are bonded to the phenyl rings, Bd) the benzotriazole derivative of the formula VI

VI

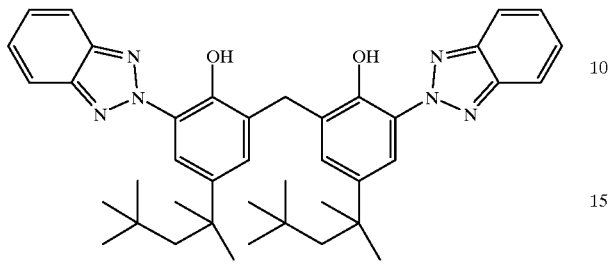

Be) the benzimidazole derivative of the formula VII

VII

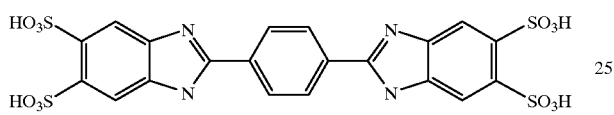

and salts

Bf) the benzotriazole derivative of the formula VIII

VIII

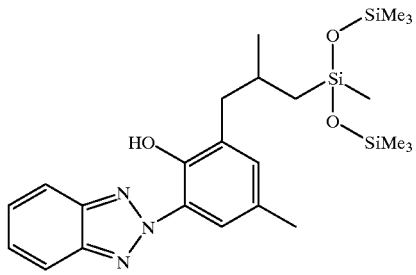

Bg) o,o',p,p'-tetrahydroxybenzophenone of the formula IX

IX

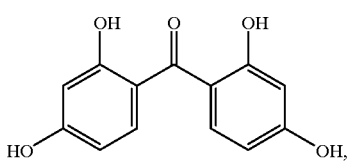

Bh) an organosiloxane benzalmalonate of the formula Xa

Xa

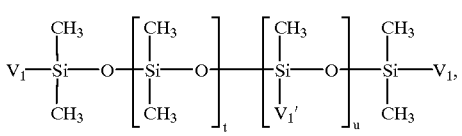

in which $V_1'$ is the group

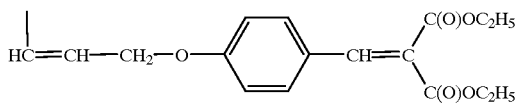

$V_1$ is a methyl group or $V_1'$, or of the formula Xb

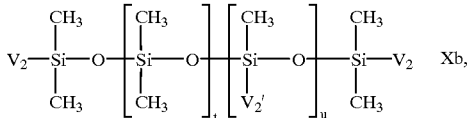

in which $V_2'$ is the group of the structure

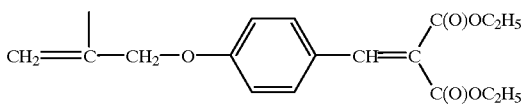

$V_2$ is a methyl group or $V_2'$ or mixtures of compounds of the formulae Xa and Xb, where t is a value up to 100 and u is a value up to 20, with the proviso that u=0, when $V_1=V_1'$ and/or $V_2=V_2'$, and u is a value from 1 to 20, when $V_1=CH_3$ and/or $V_2=CH_3$, optionally together with further compounds which absorb in the UV-A and UV-B region and which are known per se for cosmetic and pharmaceutical preparations, as sunscreens, where the UV-A-absorbing compounds are generally used in a lesser amount than the UV-B-absorbing compounds.

The sunscreen-containing cosmetic and pharmaceutical preparations are, as a rule, based on a carrier which comprises at least one oil phase. However, preparations based exclusively on water are also possible if compounds having hydrophilic substituents are used. Accordingly, oils, oil-in-water and water-in-oil emulsions, creams and pastes, protective lipstick compositions or fat-free gels are suitable.

Suitable emulsions are inter alia also O/W macroemulsions, O/W microemulsions or O/W/O emulsions containing amino-substituted hydroxybenzophenones of the formula I in dispersed form, the emulsions being obtainable by phase inversion technology, as in DE-A-197 26 121.

Conventional cosmetic auxiliaries which may be suitable as additives are, for example, coemulsifiers, fats and waxes, stabilizers, thickeners, biogenic active substances, film formers, fragrances, dyes, pearlizing agents, preservatives, pigments, electrolytes (e.g. magnesium sulfate) and pH regulators. Suitable and preferred coemulsifiers are known W/O and O/W emulsifiers such as polyglycerol esters, sorbitan esters or partially esterified glycerides. Typical examples of fats are glycerides; waxes which may be mentioned are, inter alia, beeswax, paraffin wax or microwaxes, possibly combined with hydrophilic waxes. Stabilizers which can be employed are metal salts of fatty acids such as, for example, magnesium, aluminum and/or zinc stearate. Examples of suitable thickeners are crosslinked polyacrylic acids and derivatives thereof: polysaccharides, in particular xanthan gum, guar guar, agar agar, alginates and tyloses, carboxymethylcellulose and hydroxyethylcellulose, also fatty alcohols, monoglycerides and fatty acids, polyacrylates, polyvinyl alcohol and polyvinylpyrrolidone. Examples of biogenic active substances are plant extracts, protein hydrolysates and vitamin complexes. Examples of customary film formers are hydrocolloids such as chitosan, microcrystalline chitosan or quaternized chitosan, polyvinylpyrrolidone, vinylpyrrolidone/vinyl acetate copolymers, polymers of the acrylic acid series, quaternary cellulose derivatives and similar compounds. Examples of suitable preservatives are formaldehyde solution, p-hydroxybenzoate or sorbic acid. Examples of suitable pearlizing agents are glycol distearic esters such as ethylene glycol distearate, but also fatty acids and fatty acid monoglycol esters. Dyes which can be used are the substances suitable and approved for cosmetic purposes, as listed, for example, in the publication "Kosmetische F ärbemittel" [Cosmetic Colorants] from the Farbstoffkommission der Deutschen Forschungsgemeinschaft [Dyes Commission of the German Research Society], published by Verlag Chemie, Weinheim, 1984. These dyes are normally employed in a concentration of from 0.001 to 0.1%, based on the total weight of the mixture.

An additional content of antioxidants is generally preferred. Thus, it is possible to use as favorable antioxidants all antioxidants which are customary or suitable for cosmetic and/or dermatological applications.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thiorodoxin, glutathione, cysteine, cystine, cystamine and the glycosyl, N-acetyl, methyl, ethyl, propyl, amyl, butyl, and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximines, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives thereof (e.g. ascorbyl palmitate, Mg ascorbylphosphate, ascorbylacetate), tocopherol and derivatives (e.g. vitamin E acetate, tocotrienol), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide).

The amount of the abovementioned antioxidants (one or more compounds) in the preparations is preferably from 0.001 to 30% by weight, particularly preferably from 0.05 to 20% by weight, in particular from 1 to 10% by weight, based on the total weight of the preparation.

If vitamin E and/or derivatives thereof are used as the antioxidant(s), it is advantageous to choose their particular concentration from the range 0.001 to 10% by weight, based on the total weight of the formulation.

If vitamin A and/or derivatives thereof, or carotenoids are the antioxidant(s), it is advantageous to choose their particular concentration from the range 0.001 to 10% by weight, based on the total weight of the formulation.

Customary oil components in cosmetics are, for example, paraffin oil, glyceryl stearate, isopropyl myristate, diisopropyl adipate, cetylstearyl 2-ethylhexanoate, hydrogenated polyisobutene, vaseline, caprylic/capric triglycerides, microcrystalline wax, lanolin and stearic acid.

The total amount of auxiliaries and additives can be from 1 to 80% by weight, preferably from 6 to 40% by weight, and the nonaqueous content ("active substance") can be from 20 to 80% by weight, preferably from 30 to 70% by weight, based on the compositions. The compositions can be prepared in a manner known per se, i.e. for example by hot, cold, hot-hot/cold or PIT emulsification. This is a purely mechanical process; no chemical reaction takes place.

Such sunscreen preparations can accordingly be in liquid, paste or solid form, for example as water-in-oil creams, oil-in-water creams and lotions, aerosol foam creams, gels, oils, marking pencils, powders, sprays or alcoholic-aqueous lotions.

Finally, it is also possible to co-use other substances which absorb in the UV region and are known per se provided they are stable in the overall system of the combination of UV filters to be used according to the invention.

Suitable UV filter substances which can be additionally used with the sunscreen combinations to be used according to the invention are any UV-A and UV-B filter substances. Examples which may be mentioned are:

| No. | Substance | CAS No. (= acid) |
|---|---|---|
| 1 | 4-Aminobenzoic acid | 150-13-0 |
| 2 | 3-(4-Trimethylammonium)benzylidenebornan-2-one methylsulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)-bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-Sulfo)benzylidenebornan-2-one and salts | 58030-58-6 |
| 14 | 3-Benzylidenebornan-2-one | 16087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 2,4,6-Trianiline(o-carbo-2'-ethylhexyl-1'-oxy)-1,3,5-triazine | 88122-99-0 |
| 18 | 3-Imidazol-4-yl-acrylic acid and its ethyl ester | 104-98-3 |
| 19 | Ethyl 2-cyano-3,3-diphenylacrylate | 5232-99-5 |
| 20 | 2'-Ethylhexyl 2-cyano-3,3-diphenylacrylate | 6197-30-4 |
| 21 | Menthyl o-aminobenzoate or: 5-methyl-2-(1-methylethyl) 2-aminobenzoate | 134-09-8 |

-continued

| No. | Substance | CAS No. (= acid) |
|---|---|---|
| 22 | Glyceryl p-aminobenzoate or: 1-glyceryl 4-aminobenzoate | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (mexenone) | 1641-17-4 |
| 25 | Triethanolamine salicylate | 2174-16-5 |
| 26 | Dimethoxyphenylglyoxalic acid or: sodium 3,4-dimethoxyphenylglyoxalate | 4732-70-1 |
| 27 | 3-(4-Sulfo)benzylidenebornan-2-one and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |
| 30 | 2,2'-Methylenebis-[6(2H-benzotriazol-2-yl)-4-(1,1,3,3,-tetramethylbutyl)phenol] | 103597-45-1 |
| 31 | 2,2'-(1,4-Phenylene)-bis-1H-benzimidazole-4,6-disulfonic acid, Na salt | 180898-37-7 |
| 32 | 2,4-bis-[4-(2-Ethylhexyloxy)-2-hydroxy]phenyl-6-(4-methoxyphenyl)-(1,3,5)triazine | 187393-00-6 |

The cosmetic and dermatological preparations according to the invention can advantageously further comprise inorganic pigments based on metal oxides and/or other metal compounds which are insoluble or virtually insoluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and admixtures of such oxides. Particular preference is given to pigments based on $TiO_2$ and ZnO.

For the purposes of the present invention, it is particularly advantageous, but not obligatory, for the inorganic pigments to be present in hydrophobic form, i.e. to have been surface-treated to repel water. This surface treatment can involve providing the pigments with a thin hydrophobic layer in a manner known per se, as described in DE-A-33 14 742.

To protect human hair against UV rays, the suncreen combinations to be used according to the invention can be incorporated into shampoos, lotions, gels, hairsprays, aerosol foam creams or emulsions in concentrations of from 0.1 to 10% by weight, preferably from 1 to 7% by weight. The respective formulations can be used, inter alia, for washing, coloring and for styling the hair.

The sunscreen combinations to be used according to the invention are readily soluble in cosmetic oils and can be easily incorporated into cosmetic formulations. The emulsions prepared with the novel sunscreen combinations are notable in particular for their high stability, the sunscreen combinations themselves for their high photostability, and the preparations prepared with the sunscreen combinations for their pleasant feel on the skin.

The UV filter action of the sunscreen combinations to be used according to the invention can also be utilized for stabilizing active ingredients and auxiliaries in cosmetic and pharmaceutical formulations.

The examples below illustrate the use of the novel sunscreen combinations in more detail.

EXAMPLES

Example 1

Standardized method to determine photostability (sun test)

A 5% by weight alcoholic solution of the sunscreen to be tested is applied, using an Eppendorf pipette (20 μl), to the milled area on a small glass plate. Owing to the presence of the alcohol, the solution distributes uniformly on the roughened glass surface. The amount applied corresponds to the amount of sunscreen required to obtain an average sun protection factor in sun creams. In the test, 4 small glass plates are irradiated each time. The evaporation time and the irradiation each last for 30 minutes. The glass plates are cooled slightly during the irradiation by a water cooling system located at the base of the sun test apparatus. The temperature inside the sun test apparatus during the irradiation is 40° C. After the samples have been irradiated, they are washed with ethanol into a dark 50 ml graduated flask and measured using a photometer. The blank samples are applied in the same way to small glass plates and evaporated at room temperature for 30 minutes. Like the other samples, they are washed off with ethanol and diluted to 100 ml and measured.

General procedure for preparing emulsions for cosmetic purposes

All of the oil-soluble constituents are heated to 85° C. in a stirred vessel. When all the constituents are molten or are present as liquid phase, the aqueous phase is incorporated with homogenization. The emulsion is cooled to about 40° C. with stirring, is perfumed and homogenized, and is then cooled to 25° C. with continuous stirring.

Preparations
Mass content (% by weight)

Example 2 - Lip care composition ad 100 Eucerinum anhydricum
10.00 glycerol
10.00 titanium dioxide, micronized
5.00 compound combination of 1% of Aa (formula I, R = n-hexyl), 1% of Bb (formula IVa) and 3% of Bd (formula VI)
8.00 octyl methoxycinnamate
5.00 zinc oxide
4.00 castor oil
4.00 pentaerythrityl stearate/caprate/caprylate/adipate
3,00 glyceryl stearate SE
2.00 beeswax
2.00 microcrystalline wax
2.00 quaternium-18 bentonite
1.50 PEG-45/dodecyl glycol copolymer Example 3 - Lip care composition ad 100 Eucerinum anhydricum
10.00 glycerol
10.00 titanium dioxide, micronized
5.00 compound combination of 1% of Aa (formula I, R = n-hexyl), 1% of Ab (formula II, R = neopentyl) and 3% of Bd (formula VI)
8.00 octyl methoxycinnamate
5.00 zinc oxide
4.00 castor oil
4.00 pentaerythrityl stearate/caprate/caprylate/adipate
3.00 glyceryl stearate SE
2.00 beeswax
2.00 microcrystalline wax
2.00 quaternium-18 bentonite
1.50 PEG-45/dodecyl glycol copolymer Example 4 - Sunblocker composition containing micropigments ad 100 water
10.00 octyl methoxycinnamate
6.00 PEG-7 hydrogenated castor oil
6.00 titanium dioxide, micronized
5.00 compound combination of 2% of Aa (formula I, R = n-hexyl), 1% of Bb (formula IVa) and 2% of Bd (formula VI)
5.00 mineral oil -continued Preparations
Mass content (% by weight)

5.00 isoamyl p-methoxycinnamate
5.00 propylene glycol
3.00 jojoba oil
3.00 4-methylbenzylidenecamphor
2.00 PEG-45/dodecyl glycol copolymer
1.00 dimethicone
0.50 PEG-40 hydrogenated castor oil
0.50 tocopheryl acetate
0.50 phenoxyethanol
0.20 EDTA Example 5 - Sunblocker composition containing micropigments ad 100 water
10.00 octyl methoxycinnamate
6.00 PEG-7 hydrogenated castor oil
6.00 titanium dioxide, micronized
5.00 compound combination consisting of 1.5% of Aa (formula I, R = n-hexyl), 1% of Ab (formula II, R = neopentyl) and 2.5% of Bb (formula IVb)
5.00 mineral oil
5.00 isoamyl p-methoxycinnamate
5.00 propylene glycol
3.00 jojoba oil
3.00 4-methylbenzylidenecamphor
2.00 PEG-45/dodecyl glycol copolymer
1.00 dimethicone
0.50 PEG-40 hydrogenated castor oil
0.50 tocopheryl acetate
0.50 phenoxyethanol
0.20 EDTA Example 6 - Non-greasy gel ad 100 water
8.00 octyl methoxycinnamate
7.00 titanium dioxide, micronized
5.00 compound combination consisting of 1% of Aa (formula I, R = n-hexyl), 2% of Bf (formula VIII) and 2% of Bc (formula Vb)
5.00 glycerol
5.00 PEG-25 PABA
1.00 4-methylbenzylidenecamphor
0.40 acrylate $C_{10}$–$C_{30}$ alkyl acrylate crosspolymer
0.30 imidazolidinylurea
0.25 hydroxyethylcellulose
0.25 sodium methylparaben
0.20 disodium EDTA
0.15 fragrance
0.15 sodium propylparaben
0.10 sodium hydroxide Example 7 - Non-greasy gel ad 100 water
8.00 octyl methoxycinnamate
7.00 titanium dioxide, micronized
5.00 compound combination consisting of 1% of Aa (formula I, R = n-hexyl), 1% of Ab (formula II, R = neopentyl) and 3% of Bf (formula VIII)
5.00 glycerol
5.00 PEG-25 PABA
1.00 4-methylbenzylidenecamphor
0.40 acrylate $C_{10}$–$C_{30}$ alkyl acrylate crosspolymer
0.30 imidazolidinylurea
0.25 hydroxyethylcellulose
0.25 sodium methylparaben
0.20 disodium EDTA
0.15 fragrance
0.15 sodium propylparaben
0.10 sodium hydroxide Example 8 - Sun cream ad 100 water
8.00 octyl methoxycinnamate
8.00 titanium dioxide, micronized
6.00 PEG-7-hydrogenated castor oil -continued Preparations
Mass content (% by weight)

5.00 compound combination consisting of 1.5% of Aa (formula I, R = n-hexyl), 1.5% of Bg (formula IX) and 2% of Bb (formula IVb)
6.00 mineral oil
5.00 zinc oxide
5.00 isopropyl palmitate
0.30 imidazolidinylurea
3.00 jojoba oil
2.00 PEG-45/dodecyl glycol copolymer
1.00 4-methylbenzylidenecamphor
0.60 magnesium stearate
0.50 tocopheryl acetate
0.25 methylparaben
0.20 disodium EDTA
0.15 propylparaben Example 9 - Sun cream ad 100 water
8.00 octyl methoxycinnamate
8.00 titanium dioxide, micronized
6.00 PEG-7 hydrogenated castor oil
5.00 compound combination consisting of 2% of Aa (formula I, R = n-hexyl), 1% of Be (formula VII) and 2% of Bc (formula Vb)
6.00 mineral oil
5.00 zinc oxide
5.00 isopropyl palmitate
0.30 imidazolidinylurea
3.00 jojoba oil
2.00 PEG-45/dodecyl glycol copolymer
1.00 4-methylbenzylidenecamphor
0.60 magnesium stearate
0.50 tocopheryl acetate
0.25 methylparaben
0.20 disodium EDTA
0.15 propylparaben Example 10 - Water-resistant sun cream ad 100 water
8.00 octyl methoxycinnamate
5.00 PEG-7 hydrogenated castor oil
5.00 propylene glycol
4.00 isopropyl palmitate
4.00 caprylic/capric triglyceride
5.00 compound combination consisting of 1% of Aa (formula I, R = n-hexyl), 1% of Ab (formula II, R = neopentyl), 1% of Bb (formula IVa) and 2% of Bd (formula VI)
4.00 glycerol
3.00 jojoba oil
2.00 4-methylbenzylidenecamphor
2.00 titanium dioxide, micronized
1.50 PEG-45/dodecyl glycol copolymer
1.50 dimethicone
0.70 magnesium sulfate
0.50 magnesium stearate
0.15 fragrance Example 11 - Water-resistant sun cream ad 100 water
8.00 octyl methoxycinnamate
5.00 PEG-7 hydrogenated castor oil
5.00 propylene glycol
4.00 isopropyl palmitate
4.00 caprylic/capric triglyceride
5.00 compound combination consisting of 1% of Aa (formula I, R = n-hexyl), 1% of Bb (formula IVa), 1% of Ba (formula III, $R_6$ = tert-butyl, $R_7$ = methoxy), 2% of Bb (formula IVb)
4.00 glycerol
3.00 jojoba oil
2.00 4-methylbenzylidenecamphor
2.00 titanium dioxide, micronized
1.50 PEG-45/dodecyl glycol copolymer
1.50 dimethicone
0.70 magnesium sulfate
0.50 magnesium Stearate -continued

| Preparations Mass content (% by weight) | |
|---|---|
| 0.15 | fragrance |

Example 12 - Sun milk

| ad 100 | water |
|---|---|
| 10.00 | mineral oil |
| 6.00 | PEG-7 hydrogenated castor oil |
| 5.00 | isopropyl palmitate |
| 3.50 | octyl methoxycinnamate |
| 5.00 | compound combination consisting of 1% of Aa (formula I, R = n-hexyl) and 4% of Bb (formula IVb) |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 3.00 | glycerol |
| 0.25 | methylparaben |
| 0.15 | propylparaben |
| 0.05 | tocopherol |

Example 13 - Sun milk

| ad 100 | water |
|---|---|
| 10.00 | mineral oil |
| 6.00 | PEG-7 hydrogenated castor oil |
| 5.00 | isopropyl palmitate |
| 3.50 | octyl methoxycinnamate |
| 5.00 | compound combination consisting of 0.5% of Aa (formula I, R = n-hexyl), 1% of Bb (formula IVa) and 3.5% of Bc (formula Vb) |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 3.00 | glycerol |
| 0.25 | methylparaben |
| 0.15 | propylparaben |
| 0.05 | tocopherol |

We claim:

1. A method for protecting human skin or human hair against solar rays, comprising application, to the human skin or human hair to be protected, of an effective amount of a cosmetic or pharmaceutical preparation of sunscreen combinations comprising
A) compounds absorbing essentially in the UV-A region and
B) further compounds absorbing in the UV-A region, in the UV-B region and over both regions, where the constituents (A) absorbing in the UV-A region comprise effective amounts of at least
Aa) one hydroxybenzophenone of the formula I

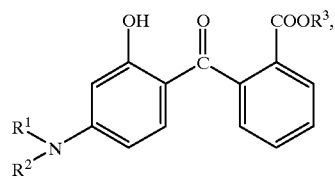

in which
$R^1$ and $R^2$ independently of one another are hydrogen, $C_1$–$C_{20}$-alkyl, $C_3$–$C_{10}$-cycloalkyl or $C_3$–$C_{10}$-cycloalkenyl, where the substituents $R^1$ and $R^2$, together with the nitrogen atom to which they are bonded, can form a 5- or 6-membered ring and
$R^3$ is $C_1$–$C_{20}$-alkyl
and optionally additionally
Ab) 4,4'-diarylbutadienes of the formula II

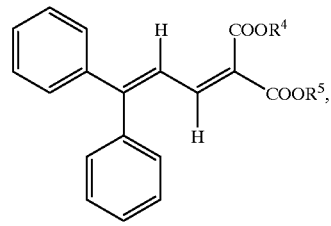

in which
$R^4$ and $R^5$ independently of one another are hydrogen, $C_1$–$C_{20}$-alkyl, $C_3$–$C_{10}$-cycloalkyl or $C_3$–$C_{10}$-cycloalkenyl,
and as compounds
B) comprise effective amounts of at least one compound chosen from the group consisting of
Ba) dibenzoylmethane compounds of the formula III

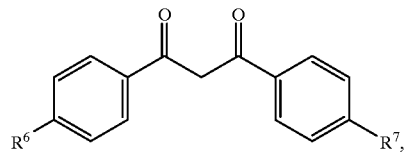

in which
$R^6$ is $C_1$–$C_{12}$-alkyl and
$R^7$ is hydrogen, $C_1$–$C_{12}$-alkyl or $C_1$–$C_{12}$-alkoxy,
Bb) triazine derivatives of the formula IV

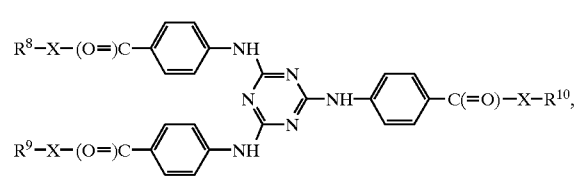

in which
$R^8$ to $R^{10}$ independently of one another are optionally substituted $C_1$–$C_{20}$-alkyl, $C_5$–$C_{10}$-aryl, $C_5$–$C_{10}$-heteroaryl or SpSil, where Sp is a spacer and Sil is a silane, oligosiloxane or polysiloxane radical,
X is the divalent radical
—O— or

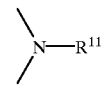

where
R$^{11}$ is hydrogen or optionally substituted C$_1$–C$_{20}$-alkyl, C$_5$–C$_{10}$-aryl or C$_5$–C$_{10}$-heteroaryl, Bc) triazine derivatives of the formula V

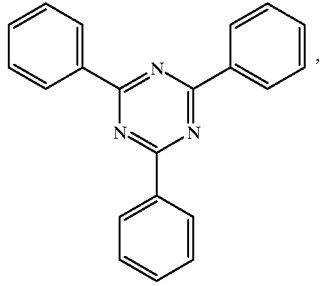

V in which at least one o-hydroxyl group and at least one p-alkoxy group having 1 to 20 carbon atoms are bonded to the phenyl rings, Bd) the benzotriazole derivative of the formula VI

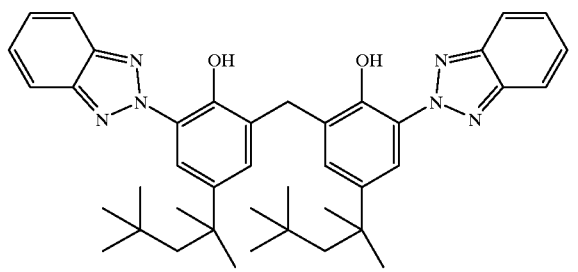

VI

Be) the benzimidazole derivative of the formula VII

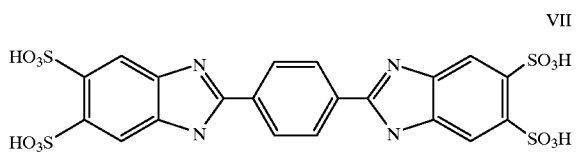

VII

Bf) the benzotriazole derivative of the formula VIII

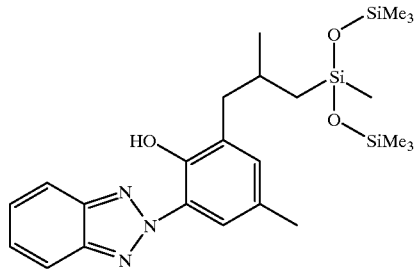

VIII

Bg) o,o',p,p'-tetrahydroxybenzophenone of the formula IX

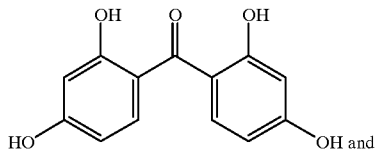

IX

Bh) an organosiloxane benzalmalonate of the formula Xa

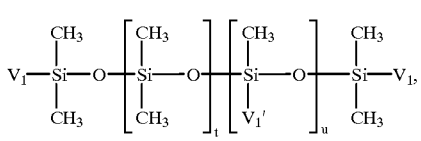

Xa in which
V$_1$' is the group

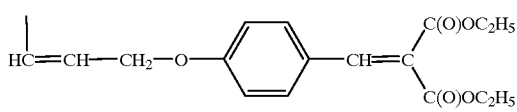

V$_1$ is a methyl group or V$_1$', or of the formula Xb

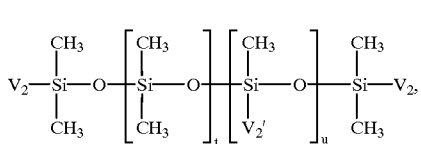

Xb in which V$_2$' is the group of the structure

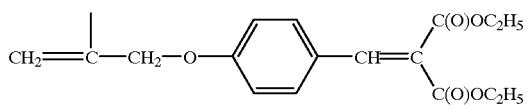

V$_2$ is a methyl group or V$_2$',
or mixtures of compounds of the formulae Xa and Xb, where t is a value up to 100 and u is a value up to 20, with the proviso that u=0, when V$_1$=V$_1$' and/or V$_2$=V$_2$', and u is a value from 1 to 20, when V$_1$=CH$_3$ and/or V$_2$=CH$_3$,
as photostable UV filters, optionally together with other compounds which absorb in the UV region and which are known per se for cosmetic and pharmaceutical preparations.

2. The method of claim 1, wherein the sunscreen combinations comprise, as essential constituent A), hydroxybenzophenone of the formula I as claimed in claim 1, in which R$^3$ is n-hexyl.

3. The method of claim 1, wherein the sunscreen combinations comprise compounds of the formula II in which R$^4$ and/or R$^5$ is neopentyl.

4. The method of claim 1, wherein the sunscreen combinations comprise, as constituent Bb), triazine derivatives of the formula IV in which the radicals —X—$R^8$ to —X—$R^{10}$ are 2-ethylhexyloxy.

5. The method of claim 1, wherein the sunscreen combinations comprise, as constituent Bb), triazine derivatives of the formula IV in which the radical —X—$R^8$ is t-butylamino and —X—$R^9$ and —X—$R^{10}$ are the radical 2-ethylhexyloxy.

6. The method of claim 1, wherein the sunscreen combinations comprise the essential constituent Aa) of the formula I in amounts of at least 5% by weight, based on the sunscreen combination.

7. The method of claim 1, wherein the sunscreen combinations comprise additionally to B) pigments in the form of zinc oxide or titanium dioxide.

8. A cosmetic or pharmaceutical preparation comprising sunscreen combinations for the protection of the human epidermis or human hair against UV light in the range from 280 to 400 nm, which comprises, in a cosmetically and pharmaceutically suitable carrier, as photostable UV filters, effective amounts of sunscreen combinations which have
A) compounds absorbing essentially in the UV-A region and
B) further compounds absorbing in the UV-A region, in the UV-B region and over both regions,
where the constituents (A) absorbing in the UV-A region comprise effective amounts of at least
Aa) one hydroxybenzophenone of the formula I

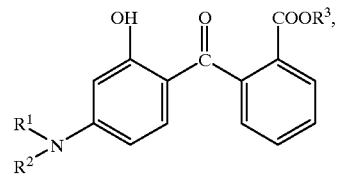

I in which
$R^1$ and $R^2$ independently of one another are hydrogen, $C_1$–$C_{20}$-alkyl, $C_3$–$C_{10}$-cycloalkyl or $C_3$–$C_{10}$-cycloalkenyl, where the substituents $R^1$ and $R^2$, together with the nitrogen atom to which they are bonded, can form a 5- or 6-membered ring and
$R^3$ is $C_1$–$C_{20}$-alkyl
and optionally additionally
Ab) 4,4'-diarylbutadienes of the formula II

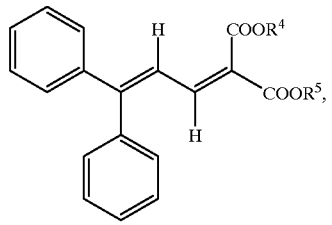

II in which
$R^4$ and $R^5$ independently of one another are hydrogen, $C_1$–$C_{20}$-alkyl, $C_3$–$C_{10}$-cycloalkyl or $C_3$–$C_{10}$-cycloalkenyl
and the constituents
B) have an effective amount of at least one compound chosen from the group consisting of
Ba) dibenzoylmethane compounds of the formula III

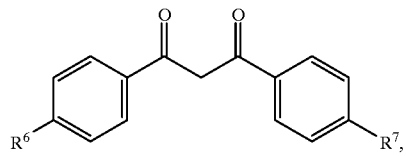

III in which
$R^6$ is $C_1$–$C_{12}$-alkyl and
$R^7$ is hydrogen, $C_1$–$C_{12}$-alkyl or $C_1$–$C_{12}$-alkoxy,
Bb) triazine derivatives of the formula IV

IV

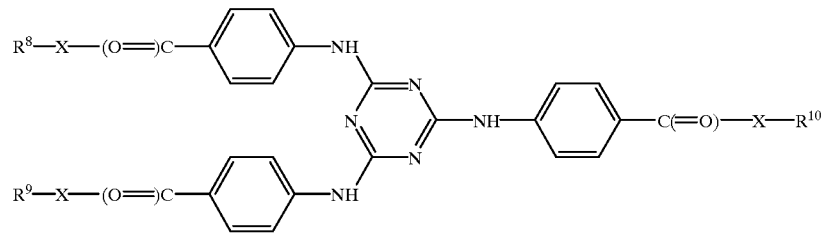

in which

R⁸ to R¹⁰ independently of one another are optionally substituted $C_1$–$C_{20}$-alkyl, $C_5$–$C_{10}$-aryl, $C_5$–$C_{10}$-heteroaryl or SpSil, where Sp is a spacer and Sil is a silane, oligosiloxane or polysiloxane radical, X is the divalent radical —O— or

where

R¹¹ is hydrogen or optionally substituted $C_1$–$C_{20}$-alkyl, $C_5$–$C_{10}$-aryl or $C_5$–$C_{10}$-heteroaryl, Bc) triazine derivatives of the formula V

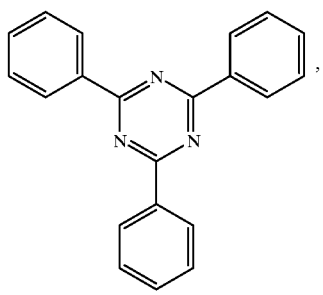

in which at least one o-hydroxyl group and at least one p-alkoxy group having 1 to 20 carbon atoms are bonded to the phenyl rings, Bd) the benzotriazole derivative of the formula VI

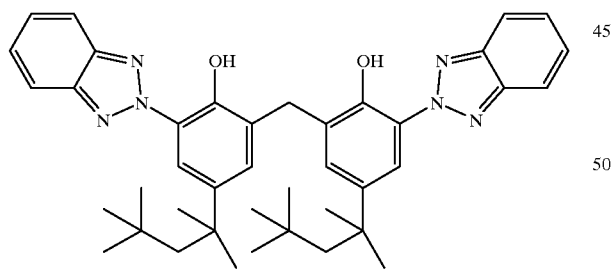

Be) the benzimidazole derivative of the formula VII

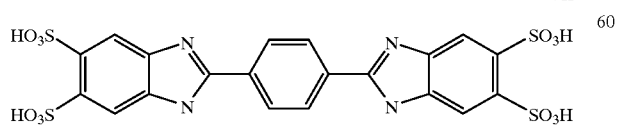

and salts

Bf) the benzotriazole derivative of the formula VIII

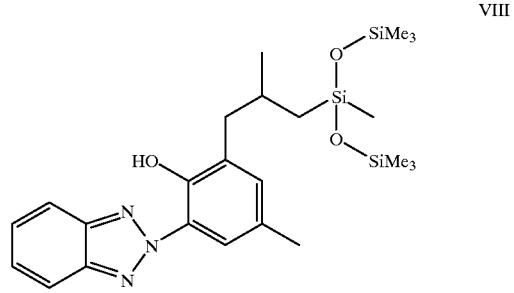

Bg) o,o',p,p'-tetrahydroxybenzophenone of the formula IX

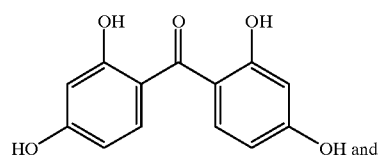

Bh) an organosiloxane benzalmalonate of the formula Xa

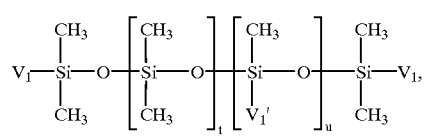

in which $V_1'$ is the group

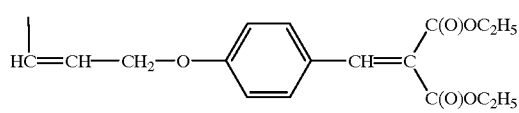

$V_1$ is a methyl group or $V_1'$, or of the formula Xb

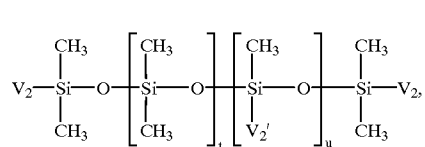

in which $V_2'$ is the group of the structure

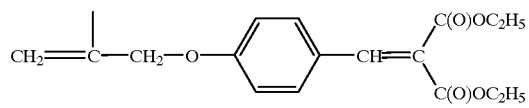

$V_2$ is a methyl group of $V_2'$ or mixtures of compounds of the formulae Xa and Xb, where t is a value up to 100 and u is a value up to 20 with the proviso that u=0, when $V_1$=$V_1'$ and/or $V_2=V_2'$, and u is a value from 1 to 20, when $V_1=CH_3$ and/or $V_2=CH_3$, as photostable UV filters in cosmetic and pharmaceutical preparations for protecting human skin or human hair against solar rays, optionally together with other compounds which absorb in the UV region and which are known per se for cosmetic and pharmaceutical preparations, optionally together with other compounds which absorb in the UV region and which are known per se for cosmetic and pharmaceutical preparations.

9. A cosmetic or pharmaceutical preparation comprising sunscreen combinations as claimed in claim 8, wherein the sunscreen combinations comprise, as essential constituent A), hydroxybenzophenone of the formula I as claimed in claim 8 in which $R^3$ is n-hexyl.

10. A cosmetic or pharmaceutical preparation comprising sunscreen combinations as claimed in claim 8, wherein the sunscreen combinations comprise compounds of the formula II in which $R^4$ and/or $R^5$ is neopentyl.

11. A cosmetic or pharmaceutical preparation comprising sunscreen combinations as claimed in claim 8, wherein the sunscreen combinations comprise, as constituent Bb), triazine derivatives of the formula IV in which the radicals —X—$R^8$ to —X—$R^{10}$ are 2-ethylhexyloxy.

12. A cosmetic or pharmaceutical preparation comprising sunscreen combinations as claimed in claim 8, wherein the sunscreen combinations comprise, as constituent Bb), triazine derivatives of the formula IV in which the radical —X—$R^8$ is t-butylamino and —X—$R^9$ and —X—$R^{10}$ are the radical 2-ethylhexyloxy.

13. A cosmetic or pharmaceutical preparation comprising sunscreen combinations as claimed in claim 8, wherein the sunscreen combinations comprise the essential constituent Aa) of the formula I in amounts of at least 5% by weight, based on the sunscreen combination.

14. A cosmetic or pharmaceutical preparation comprising sunscreen combinations as claimed in claim 8, wherein the sunscreen combinations comprise additionally to B) pigments in the form of zinc oxide or titanium dioxide.

* * * * *

UNITED STATES PATENT AND TRADEMARK OFFICE
CERTIFICATE OF CORRECTION

PATENT NO.    : 6,387,355 B2
DATED         : May 14, 2002
INVENTOR(S)   : Heidenfelder et al.

It is certified that error appears in the above-identified patent and that said Letters Patent is hereby corrected as shown below:

<u>Column 22, and Column 26,</u>
Formula IX, "OH and" should be -- OH -- and the "and" should be on the next line.

<u>Column 25,</u>
Line 66, delete "and salts".

Signed and Sealed this

Twenty-sixth Day of August, 2003

JAMES E. ROGAN
*Director of the United States Patent and Trademark Office*